United States Patent
Keen

(10) Patent No.: US 10,023,513 B1
(45) Date of Patent: Jul. 17, 2018

(54) TELOMERIZATION METHODS OF USING ETHYLENE AND/OR PROPYLENE TO MAKE TELOMERS OF LIMITED MOLECULAR WEIGHT

(71) Applicant: Brian T. Keen, Pinch, WV (US)

(72) Inventor: Brian T. Keen, Pinch, WV (US)

( * ) Notice: Subject to any disclaimer, the term of this patent is extended or adjusted under 35 U.S.C. 154(b) by 0 days.

(21) Appl. No.: 15/241,456

(22) Filed: Aug. 19, 2016

Related U.S. Application Data

(60) Provisional application No. 62/207,101, filed on Aug. 19, 2015.

(51) Int. Cl.
| | |
|---|---|
| C07C 29/44 | (2006.01) |
| C07C 2/06 | (2006.01) |
| C07C 1/22 | (2006.01) |
| C08F 110/02 | (2006.01) |

(52) U.S. Cl.
CPC ........... *C07C 29/44* (2013.01); *C07C 1/22* (2013.01); *C07C 2/06* (2013.01); *C08F 110/02* (2013.01)

(58) Field of Classification Search
CPC ... C07C 29/44; C07C 1/22; C07C 2/06; C08F 110/02
See application file for complete search history.

(56) References Cited

U.S. PATENT DOCUMENTS

| | | | |
|---|---|---|---|
| 2,402,137 A | | 8/1946 | Hanford et al. |
| 2,668,181 A | | 2/1954 | Banes et al. |
| 2,717,910 A | | 3/1955 | Erchak |
| 2,713,071 A | | 7/1955 | Erchak |
| 3,100,792 A | | 8/1963 | Emrick |
| 3,213,149 A | | 10/1965 | Takahashi et al. |
| 3,255,260 A | | 6/1966 | Anderson |
| 3,308,173 A | | 3/1967 | Emrick |
| 3,437,700 A | | 4/1969 | Niggebrugge |
| 4,156,101 A | * | 5/1979 | Erchak .................... C07C 11/02 568/715 |
| 5,068,471 A | * | 11/1991 | Paul ...................... C07C 17/278 570/137 |
| 7,977,520 B2 | | 7/2011 | Borgmann et al. |
| 8,558,030 B2 | | 10/2013 | Briggs et al. |
| 8,779,164 B2 | | 7/2014 | Leeuwen et al. |
| 8,912,346 B2 | | 12/2014 | Leeuwen et al. |
| 2003/0219903 A1 | * | 11/2003 | Wang .................... B01J 19/0093 436/37 |

FOREIGN PATENT DOCUMENTS

EP        2594546        *   5/2013

OTHER PUBLICATIONS

Jolls et al., "Computer generated phase diagrams for ethylene and propylene," Cryogenics, Jun. 1978, pp. 329-336.*
Yu-Ran Lo, "Handbook of Bond Dissociation Energies in Organic Compounds" CRC Press; 1st edition (2002), Chapter 3, pp. 11-21.
Abell et al., "Free Radicals" A Wiley-International Publication, Edited by Kochi, vol. II, Chapter XIII, C. Esters and Acids, p. 95 (1973).
Starks, "Free Radical Telomerization" Academic Press, Inc., pp. 164-165 (1974).

* cited by examiner

*Primary Examiner* — Pancham Bakshi
*Assistant Examiner* — Mark R Luderer
(74) *Attorney, Agent, or Firm* — Kagan Binder, PLLC

(57) ABSTRACT

The principles of the present invention are useful in telomerization reactions in which ethylene and/or propylene taxogen is used in free radical reactions to make telomers of limited molecular weight, e.g., those in which a major portion of the telomer products are telomers incorporating 1 to 12 moles of ethylene and/or propylene per mole of telogen (i.e., a major portion of the telomer products incorporate telomers for which n is 1 to 12). The present invention is based at least in part upon the discovery that using a very large stoichiometric excess of C1 to C12 telogen(s) (i.e., telogens incorporating 1 to 12 carbon atoms per molecule) in combination with using very low concentrations of initiator provides telomerization reactions that are selective for producing lower molecular weight telomers. In many embodiments, the present invention provides a product mixture of telomers in which a major portion of the product mixture contains telomers that incorporate 1 to 12, preferably 1 to 7, more preferably 1 to 5, even more preferably 1 to 3 moles of ethylene and/or propylene per mole of telogen.

21 Claims, No Drawings

TELOMERIZATION METHODS OF USING ETHYLENE AND/OR PROPYLENE TO MAKE TELOMERS OF LIMITED MOLECULAR WEIGHT

PRIORITY

This application claims the benefit of U.S. Provisional Patent Application Ser. No. 62/207,101, filed on Aug. 19, 2015, which is incorporated herein by reference in its entirety for all purposes.

FIELD OF THE INVENTION

The present invention relates to telomerization methods of using ethylene and/or propylene taxogens to make telomers of limited molecular weight. More specifically, the methods involve reacting ethylene and/or propylene taxogen with one or more C1 to C12 telogens (e.g., hydrocarbons, alcohols, ketones, aldehydes, esters, ethers, or combinations of these) to prepare telomers of limited molecular weight, e.g., those incorporating 1 to 12 moles of ethylene and/or propylene per mole of telogen.

BACKGROUND OF THE INVENTION

Telomerization is a chain reaction involving unsaturated compounds (monomers) and a substance that acts to propagate the reaction chain. More specifically, the term telomerization has been used to refer to a type of reaction in which one or more taxogens (i.e. one or more olefins such as ethylene, propylene, isobutylene, etc.) are reacted with one or more telogens to produce telomers according to the following schematic reaction:

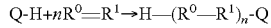

$$Q\text{-}H + nR^0 = R^1 \rightarrow H\text{---}(R^0\text{---}R^1)_n\text{-}Q$$

wherein Q typically represents a monovalent organic moiety with a structure such that the single bond between the Q and H has a bond dissociation energy often in the range from 84 kcal/mol to 98 kcal/mole, and wherein each of $R^0$ and $R^1$ independently is an organic moiety, and $R^0$ and $R^1$ are linked by a double bond. $R^0 = R^1$ schematically represents one or more unsaturated compounds comprising one or more carbon-carbon double bonds (e.g., ethylene, propylene, and other olefins in many instances); and —($R^0$—$R^1$)— schematically represents a divalent alkylene moiety corresponding to $R^0 = R^1$; and n is 1 or more. In some instances according to conventional practices, n is even 100 or more.

A telomerization reaction typically takes place in the presence of a free radical initiator. The compound Q-H is referred to as a telogen or chain transfer agent. Q-H represents a single telogen or a mixture of telogens if one more than one kind of telogen is used. The unsaturated $R^0 = R^1$ is referred to as a taxogen. The product H—($R^0$—$R^1$)$_n$-Q is a telomer. The product is often a mixture of telomers of different chain lengths, e.g., telomers characterized by a variety of n values are produced. Telomerization is further described in U.S. Pat. Nos. 8,912,346; 8,779,164; 8,558,030; and 7,977,520. Bond dissociation energies of many hydrogen bonds is reported in Yu-Ran Lo, *Handbook of Bond Dissociation Energies in Organic Compounds*, CRC Press; 1 edition (Dec. 26, 2002).

It is very desirable to produce telomer products of limited weight, those with n<12 on a weight average basis, more preferably those in which a major portion (defined below) of the product is characterized by n<12. It also is desirable to produce a substantial amount of telomer products per gram of initiator used for the reaction. Unfortunately, achieving these goals individually as well as at the same time has been challenging. For example, U.S. Pat. No. 2,668,181 describes a telomerization process that requires excessive and uneconomical amounts of costly peroxide initiator (typically 0.1 to 0.3 moles per mole of product made) and typically produces less than 10 g of product per gram of initiator. The product mix also is undesirably diffuse and relatively high molecular weight. U.S. Pat. No. 4,156,101 also describes methods that give a low product yield per 1 gram of initiator and that result in a heavy complex non-selective product mixture.

Accordingly, there is a strong need for telomerization strategies that can produce telomer products that incorporate a limited number of added taxogen molecules, while at the same time also producing increased amounts of telomer products per gram of initiator.

SUMMARY OF THE INVENTION

The principles of the present invention are useful in telomerization reactions in which ethylene and/or propylene is used in free radical reactions to make telomers of limited molecular weight, e.g., those in which a major portion of the telomer products are telomer incorporating 1 to 12 moles of ethylene and/or propylene per mole of telogen (i.e., a major portion of the telomer products incorporate telomers for which n is 1 to 12). The present invention is based at least in part upon the discovery that using a very large stoichiometric excess of C1 to C12 telogen(s) (i.e., telogens incorporating 1 to 12 carbon atoms per molecule) in combination with using very low concentrations of initiator provides telomerization reactions that are selective for producing lower molecular weight telomers. In many embodiments, the present invention provides a product mixture of telomers in which a major portion of the product mixture contains telomers that incorporate 1 to 12, preferably 1 to 7, more preferably 1 to 5, even more preferably 1 to 3 moles of ethylene and/or propylene per mole of telogen. Often times the product containing 1 mole of ethylene per mole of telogen is the product in highest percentage yield.

Although the reaction can be carried out in batch or continuous modes, continuous modes are more preferred. In batch modes, the ratios of reactants and initiator(s) tend to change as the reaction proceeds. This can make it more difficult to control the nature (e.g., the n values) of the telomer products produced by the reaction. In contrast, the ratios are much easier to control and maintain in continuous modes, making it easier to control the nature of the telomer products.

The present invention is useful with a wide variety of telogens. Examples include hydrocarbons, alcohols, aldehydes, ketones, ethers, esters, combinations of these and the like. The present invention also is useful with a variety of ethylene and/or propylene feed stocks of variable purity from a variety of sources.

In illustrative embodiments the invention involves reacting at least one alcohol such as methanol, ethanol, isopropanol and/or 2-butanol with ethylene and/or ethylene/ethane mixtures in the liquid phase in the presence of at least free radical initiator at pressures in the range from 400 psig to 2400 psig at reaction temperatures of 100° C. to 300° C. in an inert surface reactor. Higher pressures may be used, but offer little extra benefit to justify the additional cost involved unless higher pressures are desired to make it easier to conduct the reaction in a preferred liquid phase. Using higher pressures may be desirable, for instance, if significant ethane is present in the ethylene feed or if one or more ingredients in the reaction zone have a vapor pressure higher than that of ethylene.

The present invention allows the formulation of the product mixture to be easily controlled by adjusting the molar ratio of telogen to ethylene and/or propylene, the molar ratio of ethylene and/or propylene to initiator, the reaction residence time, reaction temperature, pressure, the way the reaction is conducted and if desired selective product recycle. For example, typically raising the reaction temperature raises the rate of reaction and lowers the concentration of unreacted ethylene and/or propylene exiting the reactor. This generally promotes the formation of lower molecular weight products. Similarly, using greater amounts of telogen and/or lower amounts of initiator provides processes that are also more selective for lower molecular weight products.

In some modes of practice, the present invention is useful to synthesize fuels from ethanol sources, including bioethanol. For example, ethanol from any source(s) is in part converted to ethylene, and the ethylene and ethanol may then be reacted by the process of the invention to produce a product mixture for which a major portion comprises C3 to C30 hydrocarbons and alcohols. Other exemplary modes of the invention produce fuel grade hydrocarbons from natural gas liquids and/or ethylene/ethane mixtures. Any modes of practice may involve recycle of some of the lower molecular weight products to the reaction zone.

For example, an embodiment of the present invention may involve using ethylene and methanol as reactants to make propanol (C3), pentanol (C5), heptanol (C7), and some heavier alcohols. A goal could be to make highly desired propanol as well as C7 and heavier alcohols to use as constituents of gasoline. This is easily accomplished by selective purification of product streams resulting from telomerization. For example, a series of distillation columns could be used to recover and recycle methanol; to recover product propanol, to recover and recycle C5 alcohols, and to recover a heavy product stream for use in gasoline.

A useful indicator of the efficiency of telomerization reactions is the ratio (efficiency ratio) of the total weight of the resultant telomer products to the total amount of initiator(s) supplied to the reaction. Generally, a greater ratio indicates higher efficiency. Many conventional processes are characterized by an efficiency ratio of 10 or less or even 5 or less. As a significant advantage, many methods of the present invention provide efficiency ratios of 10 or more, even 50 or more, or even 60 or more. This means that the composite weight of the resultant telomer products exceeds ten times, even fifty times or even sixty times the weight of initiator used. As a further advantage, the composite yields of telomer products typically exceeds the initiator by over tenfold and often times fifty fold by weight, even over sixty fold while producing a desirable product mixture for which a major portion (defined below) is the lower molecular weight telomers incorporating 1 to 12, preferably 1 to 7, more preferably 1 to 5, even more preferably 1 to 3 moles of ethylene and/or propylene taxogen per mole of telogen.

Also of significance, the literature suggests that chain transfer is a poor reaction strategy for an alcohol such as methanol or other reactants with C—H bond strengths in the 93 kcal/mol to 97 kcal/mol regimes (as measured at 298 K). Advantageously, the present invention provides reaction features which facilitate effective chain transfer. This is accomplished in part by using a large stoichiometric excess of telogen, using low amounts of initiator, and maintaining a high ethylene and/or propylene reaction rate in the reaction zone such that overall ethylene conversion is high (such as by running the reaction at higher temperatures or pressures, by using active initiators such as an initiator having a 10 minute to 3 hour half-life at 140° C.). Advantageously, these features help to enhance chain transfer more than would be expected according to conventional knowledge.

In one aspect, the present invention relates to a method of using ethylene and/or propylene taxogen to prepare one or more higher molecular weight compounds, comprising the step of free radically reacting reactants comprising ethylene and/or propylene taxogens and at least one C1 to C12 telogen in the presence of a free radical initiator component, wherein:
  a. the at least one C1 to C12 telogens and the ethylene and/or propylene taxogens are supplied to a reaction zone at a feed molar ratio of the telogens to the taxogens that is in the range from 2:1 to 200:1;
  b. the ethylene and/or propylene taxogens and the free radical initiator component are supplied to the reaction zone at a molar ratio of the ethylene and/or propylene taxogens to the free radical initiator component that is in the range from 8:1 to 10,000:1; and
  c. the at least one C1 to C12 telogens and the ethylene and/or propylene taxogens are present in the reaction zone at a steady state molar ratio of the telogens to the taxogens that is in the range from 10:1 to 500:1.

In another aspect, the present invention relates to a method of using ethylene and/or propylene taxogen to prepare one or more higher molecular weight compounds, comprising the step of free radically reacting reactants comprising ethylene and/or propylene taxogens and at least one C1 to C12 telogen in the presence of a free radical initiator component, wherein:
  a. the at least one C1 to C12 telogens and the ethylene and/or propylene taxogens are supplied to a reaction zone at a feed molar ratio of the telogens to the taxogens that is in the range from 2:1 to 200:1;
  b. the ethylene and/or propylene taxogens and the free radical initiator component are supplied to the reaction zone at a molar ratio of the ethylene and/or propylene taxogens to the free radical initiator component that is in the range from 8:1 to 10,000:1; and
  c. the at least one C1 to C12 telogens and the ethylene and/or propylene taxogens are present in the reaction zone at a steady state molar ratio of the telogens to the taxogens that is at least twice the feed molar ratio of the telogens to the taxogens.

In another aspect, the present invention relates to a method of preparing a compound of the formula H—(CH$_2$CH$_2$)$_n$R—OH, comprising the step of free radically reacting reactants comprising ethylene and/or propylene taxogen and one or more alcohols of the formula H—R—OH in the presence of a free radical initiator component; wherein:
  a. the one or more alcohols and the ethylene and/or propylene taxogens are supplied to a reaction zone at a feed molar ratio of the alcohols to the taxogens that is in the range from 2:1 to 200:1;
  b. the ethylene and/or propylene taxogens and the free radical initiator component are supplied to the reaction zone at a molar ratio of the ethylene and/or propylene taxogens to the free radical initiator component that is in the range from 8:1 to 10,000:1; and
  c. the one or more alcohols and the ethylene and/or propylene taxogens are present in the reaction zone at a steady state molar ratio of the alcohols to the taxogens that is in the range from 10:1 to 500:1;

d. n is in the range from 1 to 12; and e. R is a divalent organic moiety.

DETAILED DESCRIPTION OF PRESENTLY PREFERRED EMBODIMENTS

The present invention will now be further described with reference to the following illustrative embodiments. The embodiments of the present invention described below are not intended to be exhaustive or to limit the invention to the precise forms disclosed in the following detailed description. Rather a purpose of the embodiments chosen and described is so that the appreciation and understanding by others skilled in the art of the principles and practices of the present invention can be facilitated.

The principles of the present invention are useful in telomerization reactions in which ethylene and/or propylene, as taxogen(s), is/are reacted with one or more telogens (also known in this context as chain transfer agents or chain transfer molecules) in order to form a product comprising one or more resultant telomers. In many modes of practice, the product is a mixture of telomers with different chain lengths. The telomerization reactions of the present invention are carried out under conditions so that a major portion of the telomer products are telomers independently comprising 1 to 12, preferably 1 to 7, more preferably 1 to 5, even more preferably 1 to 3 moles of ethylene and/or propylene per mole of telogen. As used herein, a major portion means that at least 50 weight percent, more preferably at least 75 weight percent of the telomer products have the characteristic based upon the total weight of telomers in the product mixture.

In one aspect, the present invention provides a method of using ethylene to prepare one or more, higher molecular weight compounds. Reactants comprising at least ethylene and at least one C1 to C12 telogen are free radically reacted in the presence of a free radical initiator component.

A variety of different ethylene feedstocks may be used in the telomerization reaction in which the purity of ethylene in the feedstock may be selected from a wide range of purities. For example, in some modes of practice, the ethylene may be supplied in a relatively pure form in which the feedstock comprising ethylene includes at least 85 weight percent, preferably at least 90 weight percent, more preferably at least 95 weight percent, and even more preferably substantially 100 weight percent ethylene based on the total weight of the feedstock.

In other modes of practice, feedstock mixtures containing a lesser weight percent of ethylene may be used. For example, a substantial amount of commercially available ethylene is derived from feedstocks that, by their nature, contain both ethane and ethylene and thus are dilute in ethylene. In some instances, such feedstocks result from processes in which the nature of the chemistry causes the feedstock to include no more than about 80 weight percent ethylene based on the total weight of the feedstock. In many instances, such feedstocks may include from about 25 weight percent to about 80 weight percent ethylene based upon the total weight of the feedstock. Because ethane is substantially inert under reaction conditions used in many modes of practice, such feedstock mixtures may be used as is to carry out telomerization reactions of the present invention. Alternatively, such mixtures may be purified or partially purified to provide a feedstock that is richer in ethylene, and such purified feedstock could then be used in the practice of the present invention. It is advantageous to feed the ethylene as a mixture with its parent saturated hydrocarbon, ethane to avoid the high cost of separating ethylene from ethane. The process efficiently reacts the telogen with the ethylene without significant impact to the starting ethane. That is, ethane is essentially inert in the reaction.

The ability to use a variety of widely available ethylene feedstocks is a practical advantage. At the same time there is a shortage of $C_3$ to $C_{24}$ alcohols, hydrocarbons and oxygenated chemicals (e.g., ketones, aldehydes, esters, ethers, etc.). The present invention fills the important need of using widely available feed materials to produce products in high demand.

The preferred telogen(s) used in the telomerization reaction are organic compounds that contain 1 (C1) to 12 (C12) carbon atoms, although telogens containing more than 12 carbon atoms may be used. Telogens generally are unsaturated or saturated, and may be linear, branched, or cyclic. Telogens may be aliphatic or aromatic, but preferably are at least partially aliphatic. Telogens may be substituted (e.g., comprising a carbon backbone having pendant substituents other than H) or unsubstituted (e.g., a hydrocarbon containing a backbone having only H substituents). Telogens may include one or more heteroatomns such as O, S, P, N, combinations of these, or the like. Other olefins (if any) in addition to ethylene and/or propylene optionally that are present are deemed to be telogens.

A wide variety of compounds having 1 to 12 carbon atoms may be used as telogens in the practice of the present invention. Examples include alkanes, alcohols, ketones, aldehydes, carboxylic acids, anhydrides, ethers, combinations of these, and the like. Some telogens may comprise only a single functionality or a combination of functionalities. For example, some telogens may be diols or triols or other compounds including a plurality of hydroxyl groups. Others may include at least one ether functionality and at least one alcohol functionality. Others may include at least one ester functionality and at least one hydroxyl functionality.

In preferred modes of practice, the telogen comprises one or more alcohols of the formula H—R—OH, wherein R is a hydrocarbylene moiety comprising 1 to 12 carbon atoms. The hydroxyl groups may be primary, secondary, or tertiary. Alcohols can be reacted with ethylene via free radical telomerization to prepare telomer products of the formula H—$(CH_2CH_2)_n$—ROH, wherein a major portion of the telomer products have an n value from 1 to 12 and R is a hydrocarbylene moiety as defined herein. Examples of suitable alcohols include methanol, ethanol, isopropanol, n-butanol, 2-butanol, isobutanol, ethylene glycol, neopentyl glycol, propylene glycol, glycerol, other C5 to C12 alcohols, combinations of these, and the like.

Illustrative examples of suitable ketones useful as a telogen include acetone, 2-butanone, other C5 to C12 ketones combinations of these, and the like.

Illustrative examples of aldehydes useful as a telogen include acetaldehyde, propionaldehyde, butyraldehyde, pentanal combinations of these, and the like.

Illustrative examples of ethers useful as a telogen include ethyl ether, isopropyl ether, butyl ether, tetrahydrofuran combinations of these, and the like.

Illustrative examples of carboxylic acids and anhydrides useful as a telogen include formic acid, acetic acid, propionic acid, succinic acid, succinic anhydride, maleic anhydride, isobutyric acid combinations of these, and the like.

Illustrative examples of alkanes useful as a telogen include propane, butane, isobutane, pentane, 2-methyl butane, toluene and other C5 to C12 alkanes combinations of these and the like.

Illustrative examples of esters useful as a telogen include methyl acetate, methyl propionate, ethyl acetate, methyl benzoate, propyl propionate, butyl propionate, ethyl 3-ethoxypropionate, combinations of these, and the like.

In some embodiments, a telogen used in the practice of the present invention comprises at least one C—H bond having a bond dissociation energy of less than 97 kcal/mole. In many such embodiments, the bond dissociation energy is greater than 84 kcal/mole. Such bond dissociation energies generally mean that chain transfer is exothermic. However chain extension (telomerization) is also exothermic. The present invention provides reaction conditions that favor chain transfer over chain extension. To help control the associated exotherm, the present invention provides a high ratio of telogen to taxogen in the reaction zone. Maintaining this higher ratio is easier in continuous reaction modes. In continuous modes, the reaction is carried out in a manner to maintain a relatively low steady state concentration of ethylene and/or propylene relative to the telogen(s).

In chemistry, bond-dissociation energy (BDE) is a measure of the strength in a chemical bond. It is defined as the standard enthalpy change when a bond is cleaved by homolysis at a defined temperature. Bond disassociation energies vary to some degree with temperature, but are typically reported at 298° K or 25° C. The bond dissociation energy of C—H bonds tends to decrease with increasing substitution on the carbon. Thus, the BDE for a primary C—H bond in ethane is about 98 kcal/mole whereas the BDE for the tertiary C—H bond in $(CH_3)_3$—C—H is about 92 kcal/mole. Exemplary bond dissociation energies are reported in the following table:

Bond Disassociation Energies (Kcal Per Mole)-All Thermal Homolytic Cleavage

| Compound | Structure | Bond dissociation energy, kcal/mole, 25 C. |
| --- | --- | --- |
| Methane | $CH_3$—H | 104 |
| Ethane | $CH_3CH_2$—H | 98 |
| Propane | $(CH_3)_2CH$—H | 95 |
| Isobutane | $(CH_3)_3C$—H | 92 |
| Water | HO—H | 119 |
| Any alcohol O—H | RO—H | About 104 |
| Any aldehyde C—H | $CH_3C(O)$—H | About 86 |
| Methanol | H—$CH_2OH$ | 94 |
| Ethylene | $CH_2$=CH—H | 118 |
| Propylene | $CH_2$=$CHCH_2$—H | 89 |
| Ethanol | H—$CH(CH_3)OH$ | 93 |
| Isopropanol | H—$C(CH_3)_2OH$ | 91 |
| Hydrogen peroxide | $HO_2$—H | 51 |
| C4 peroxide | HO—$OC(CH_3)_3$ | 46 |
| C8 peroxide | $(CH_3)_3CO$—$OC(CH_3)_3$ | 38 |

Additionally, a benzylic C—H bond has a bond dissociation energy of 90 kcal/mol, which is suitable in the practice of the present invention. Additional modes of practice may use toluene (methyl benzene) as a telogen. Bond dissociation energies of many hydrogen bonds is reported in Yu-Ran Lo, *Handbook of Bond Dissociation Energies in Organic Compounds*, CRC Press; 1 edition (Dec. 26, 2002).

In the practice of the present invention, the molar ratio of the total amount of telogen reactants to the total amount of the one or more taxogen reactants as supplied to the reaction zone (the feed molar ratio) is greater than 2:1, preferably greater than 8:1 and more preferably greater than 10:1. This means that the telogen(s) as fed to the reaction zone are in a relatively large excess relative to the taxogen(s). This is an important aspect of the invention that is helpful so that telomerization results in lower molecular weight telomer products incorporating from 1 to 10, more preferably 1 to 5, even more preferably 1 to 3 alkylene residues derived from taxogens. In general, increasing the molar ratio of telogen to taxogen tends to produce a product mixture in which the average value of n is smaller. This is highly desirable when lower molecular weight telomers are more desired products.

For example, one telomer reaction product mixture is obtained by reacting ethylene with a large stoichiometric excess of ethanol. The resultant product may a telomer mixture in which a major portion of the telomers have the formula H—$(CH_2CH_2)_n$—$CH(CH_3)$—OH, wherein n is 1 to 4. In these telomers, the —$CH_2CH_2$— moieties are alkylene units that are residues of ethylene. With a major portion of the telomers being characterized by n=1 to 4, this means that this portion of the telomer product mixture includes 1 to 4 residues of ethylene.

As another example, ethylene was reacted with a large stoichiometric excess of isopropanol to form larger alcohols. After allowing the reaction to proceed for an extended period of time, about 79 weight percent of the resultant telomer products were alcohol telomers that incorporated one residue of ethylene (C5 alcohol) or two residues of ethylene (C7 alcohol). The balance of the telomer products were mostly C9 to C21 alcohols, although larger alcohol species also were present. This shows that using a large stoichiometric excess of the telogens helps to provide more selectivity for forming lower molecular weight telomers.

Additionally, the at least one C1 to C12 telogens and the ethylene and/or propylene taxogens are present in the reaction zone at a steady state molar ratio of the telogens to the taxogens that is at least twice the feed molar ratio, and preferably is in the range from 10:1 to 500:1, more preferably 20:1 to 200:1. Note that the steady state molar ratio is much higher than the feed molar ratio. This difference is important in order for the reaction zone to favor chain transfer and thereby provide a reaction strategy that favors producing lower molecular weight telomers. The steady state molar ratio is higher than the feed molar ratio because the reaction is carried out such that the molar conversion of the taxogens to telomer desirably is greater than 60 molar percent, preferably at least 75 molar percent, and even more desirably at least 90 molar percent to substantially 100 molar percent. In the meantime, the reaction is carried out so that the molar conversion of the telogens to telomers is lower such as less than 40 molar percent, preferably less than 25 molar percent, or even 0.5 to 10 molar percent. The conversion rates of the taxogen and telogen are controlled by adjusting one or more of the flow rate of the reactants, the temperature of the reaction zone, the pressure in the reaction zone, and/or the residence time in the reaction zone. For example, if conversion of the taxogen to telomer is too low, the temperature, pressure, flow rate, and/or residence time could be increased. The goal in many embodiments is to select these parameters in a manner effective to help ensure that taxogen conversion preferably is greater than 50% and more preferably greater than 80% at steady state conditions.

In illustrative modes of practice, the reaction between ethylene and at least one C1 to C12 telogen may be represented schematically by the following preferred reaction scheme:

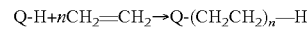

wherein Q is a monovalent, organic moiety including 1 to 12 carbon atoms, an. Taking into account that the reaction product typically comprises a mixture of telomers, a major portion of the telomer products desirably has n values in the range from 1 to 12, preferably 1 to 7, more preferably 1-5, even more preferably 1-3.

In one preferred embodiments, Q-H comprises one or more alcohols. Each alcohol independently may comprise one or more OH groups. The OH groups may be primary, secondary, or tertiary. The reaction between ethylene and at least one C1 to C12 alcohol may be represented schematically by the following preferred reaction scheme:

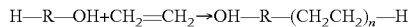

H—R—OH+CH$_2$=CH$_2$→OH—R—(CH$_2$CH$_2$)$_n$—H wherein R is a divalent organic moiety comprising 1 to 12 carbon atoms and may be linear, branched, or cyclic. R may be aliphatic and/or aromatic. R preferably is aliphatic. In some illustrative embodiments, R is a hydrocarbylene moiety. As used herein, a hydrocarbylene moiety is a divalent moiety having a carbon backbone on which H atoms are the only substituents. Hydrocarbylene moieties also are referred to as alkylene moieties. Examples include —CH(CH$_3$)—, —CH(CH$_2$CH$_3$)—, —C(CH$_3$)$_2$—, —C(CH$_3$)(CH$_2$CH$_3$)—, —C(CH$_2$)$_4$-(cyclopentanol)-, cyclohexylene (wherein the open valent sites are on the same carbon). In other illustrative embodiments, R may comprise 1 to 6 alkylene oxide units such as —CH$_2$O—, —CH$_2$CH$_2$O—, —CH(CH$_3$)CH$_2$O—, combinations of these, and the like. In other embodiments, R may include one or more heteroatoms such as O, N, S, P, combinations of these, and the like.

In other preferred embodiments, Q-H comprises one or more hydrocarbons. Each hydrocarbon may be linear, branched, or cyclic. The hydrocarbon may contain primary, secondary or tertiary carbon atoms as well as unsaturation. The reaction between ethylene and at least one C1 to C12 hydrocarbon may be represented schematically by the following preferred reaction scheme:

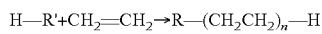

H—R'+CH$_2$=CH$_2$→R—(CH$_2$CH$_2$)$_n$—H

R' is a monovalent hydrocarbyl moiety comprising 1 to 12 carbon atoms and may be linear, branched, or cyclic. R' may be partially aliphatic and/or aromatic. R' preferably is aliphatic. Examples include —CH(CH$_3$)CH$_3$, —CH(CH$_3$)CH$_2$CH$_3$, —C(CH$_3$)$_3$, cyclohexylene, cycloheptyl and the like. The telomerization reaction occurs in the presence of a free radical initiator component. The free radical initiator component comprises one or more free radical initiators. Free radical initiators are well known in the field of free radical synthesis and are substances that can produce radical species to promote radical reactions. Illustrative examples are halogen molecules such as chlorine; azo compounds such as azobisisobutyronitrile and/or 1,1'-Azobis (cyclohexanecarbonitrile); and organic and inorganic peroxides such as di-tertiary butyl peroxide (DTBP), cumene hydroperoxide, paramenthane hydroperoxide, dicumyl peroxide, tertiary butyl hydroperoxide (TBHP), tertiary butyl peracetate, cyclohexanone peroxide, decanoyl peroxide, laurel peroxide, diisopropylperoxydicarbonate, and hydrogen peroxide. DBTP is preferred as having low induced decomposition. As a drawback, DBTP is relatively expensive. However, low amounts of free radical initiator(s) are used in the practice of the present invention so that the expense of DBTP may be an insignificant burden. TBHP also is preferred. Although more susceptible to induced composition as compared to DBTP, TBHP is much less expensive. Also, initiator(s) may be used in such low amounts in the practice of the present invention such that the risks associated with induced decomposition are reduced.

The molar ratio of the total amount of ethylene and other taxogen(s) (if any) to the total moles of one or more free radical initiators as supplied to the reaction is 8:1 or more, preferably 20:1 or more, more preferably 40:1 or more, or even 80:1 or more. In many embodiments, such molar ratio is no more than 5000:1, preferably no more than 2000:1. This means that relatively little amounts of the free radical initiator(s) are present. This is an important aspect of the invention that is helpful so that telomerization results in telomer products incorporating from 1 to 10, more preferably 1 to 5, even more preferably 1 to 3 alkylene residues derived from taxogens. The fact that so little initiator can produce such high levels of telomer products is surprising and results at least in part by maintaining reaction conditions that favor chain transfer. In general, increasing the molar ratio of taxogen(s) to the initiator(s) and running the reaction continuously at high rate tends to produce a product mixture in which the average number of alkylene residues derived from taxogens is smaller. This is highly desirable when lower molecular weight telomers are more desired.

Even though the amount of initiator used in the practice of the present invention is relatively low, the methods of the present invention still produce a substantial amount of telomer products per gram of initiator(s). For example, illustrative modes of practice may produce 100 grams or more of telomer products per 1 g of initiator.

The ability of the present methods to produce so much telomer product per g initiator is counterintuitive. Because initiator(s) are present in such low amounts, the initiators produce low concentrations of radicals in the reaction medium. Conventionally, an expectation would be that a low amount of desired telomer product would result. Without wishing to be bound by theory, a rationale to explain the high production of telomer product can be suggested. It is believed that the limited amount of taxogen (e.g., ethylene) to the telogen (e.g., alcohol), the limited amount of the initiator relative to the taxogen and running the reaction continuously at high rate produces a reaction environment in which chain transfer steps are favored. As a result, the methods of the present invention are highly selective for preparing telomer product mixtures of the formula

R—(CH$_2$CH$_2$)$_n$—H or OH—R—(CH$_2$CH$_2$)$_n$—H as described above for which a major portion of the telomer products have n values in the range from 1 to 12, preferably 1 to 7, more preferably 1 to 5, and even more preferably 1 to 3. In contrast, when chain transfer is not favored, the n values for a major portion of the telomer products tend to be much higher, e.g., >15 or more, or even >30 or more.

Another aspect of the present invention that helps to provide selectivity for lower n values is that the reaction is carried out in a manner such that the ethylene and other taxogens, if any, are converted at high yield to telomer products, but the telogen reactants are converted to telomer products at relatively low yield. For example, it is suitable to carry out the reaction so that 3 to 15 weight percent of the total amount of telogen reactant is converted into the desired telomers. This strategy also helps to minimize production of undue amounts of by-products. Additionally, the telomerization reaction tends to be exothermic in many instances. Running the reaction at low conversion of telogen makes it easier to help prevent too much energy being released during the reaction. The lower yield is not problematic in terms of overall efficiency, because unreacted telogen reactant optionally can be recycled back to the reaction zone after separating the unreacted telogen from the product mixture.

The reaction may occur within a wide temperature range. If the temperature is too low, the reaction may take too long to proceed to the desired degree of conversion and/or selectivity. If the temperature is too hot, undue amounts of by-products may result and/or the risk of thermal degradation of reactants or products increases. Balancing such concerns, the reaction desirably occurs in the range from 100 C to 300 C, preferably 150° C. to 250° C. Optionally, the reaction may occur in one or more temperature stages. For example, an initial portion of the reaction may occur at a first temperature or temperature range such as at a temperature in the range from 130° C. to 200° C. Then, a subsequent portion of the reaction may occur at a second temperature or temperature range such as at a temperature in the range from 200° C. to 250° C.

Metal materials include pure metals, metal alloys, intermetallic compositions, metal ions, some metal salts and the like. Metal materials can quench the desired reaction such as by promoting radical chain termination via a disproportionation reaction. Metals and metal salts are believed to do this by converting carbon radicals to positive ions via electron transfer processes. Metal oxides, carbides and nitrides incorporating easily oxidized or easily reduced metal constituents (e.g., transition metals such as Fe) also can quench the desired reaction via similar mechanisms. Examples of such compounds include ferric oxide, ferrous oxide, ferric chloride, combinations of these and the like. Accordingly it is desirable to minimize or even exclude metal materials and such transition metal oxides from the reaction zone in which the reaction is occurring as much as is practicable. It is particularly desirable to minimize or exclude metals, especially easily oxidized or easily reduced metal ions in the reaction zone in the practice of the present invention where the initiator is present at relatively low concentrations relative to the reactants.

Minimizing or excluding metals from the reaction zone can be accomplished in different ways. A first approach is to carry out the reaction in a reaction zone whose surfaces in contact with the reaction materials are substantially inert with respect to the reactants, reaction products, oxidation, reduction, and reaction by-products (if any). A wide range of such inert surfaces may be used. Examples of materials useful to form inert surfaces include fluropolymers such as polytetrafluoroethylene (PTFE), glass such as quartz, and some ceramic materials such as oxides, nitrides, or carbides combinations of these and the like that contain minimal amounts, e.g., under 10 weight percent, preferably under 3 weight percent, more preferably under 0.5 weight percent of transition metals based on the total weight of the materials. Reactor vessels with PTFE walls or PTFE-lined walls are preferred. PTFE is available under the trade designation TEFLON from E. I. Du Pont de Nemours.

Another approach to minimize contact between metal materials and the reaction medium is to carry out the reaction in a vessel whose reaction volume is sufficiently high so that the reaction volume is relatively large compared to the surface areas of the surfaces that define the reaction volume. This can be accomplished, for example, using reactor vessels (e.g., cylindrical reactors) with volumes of at least about 20 liters, more preferably at least about 400 liters.

Another approach is to carry out the reaction under conditions such that the reaction proceeds to the desired degree of completion in a relatively short time, e.g., 1 to 60 minutes. This can be accomplished by carrying out the reaction at higher temperatures, e.g., 170° C. to 230° C. Reactants can be separately pre-heated to near the desired reaction temperature before being combined to further help shorten residence time in the reactor.

The reaction may be carried out at one or more pressures selected from a wide range. If the pressure is too low, then it may be harder to keep ethylene in the reaction zone. If the pressure is too high, then reactor operation costs maybe high. As illustrative guidelines, the reaction may be carried out a pressure from 400 psig to 2400 psig, preferably 700 psig to 1500 psig. Higher pressures may be used, but offer little added benefit but involve more procedural and equipment expense. In some embodiments, it has been found that running at reaction pressures in the 700 psi to 2000 psi range and at temperatures 160° C. to 230° C. helps to ensure sufficient, but not excessive, ethylene availability and high chain transfer efficiency.

Generally, it is desirable to exclude oxygen from the reaction unless oxygen is being used to generate peroxide. Accordingly, it is desirable to carry out the reaction in the absence of a headspace or optionally in the presence of at least one inert gas such as $N_2$, He, Ar, $CO_2$, combinations of these, or the like. Optionally, the reactants and initiators may be de-gassed prior to use in the reaction. As a further option, the reactants and initiators may be dried prior to use in the reaction as well so that the ingredients as supplied to the reaction have a reduced moisture content of 0 weight percent to 1 weight percent, more preferably 0 weight percent to 0.1 weight percent based on the total weight of reactants and initiator.

Without wishing to be bound by theory, it is believed that the free radical reaction between the taxogen and telogen proceeds by a multi-step pathway including initiation, propagation, and termination steps. For example, one mode of practice involves reacting ethylene as taxogen with ethanol as the telogen in the presence of the initiator DTBP. The overall reaction may be represented by the following:

$$CH_3CH_2OH + nCH_2=CH_2 \rightarrow H-(CH_2CH_2)_n-CH(CH_3)OH$$

wherein a major portion of the telomer products have an n value in the range from 1 to 12, preferably 1 to 7, more preferably 1 to 5, even more preferably 1 to 3.

Without wishing to be bound, the reaction pathway steps for the overall reaction for ethanol and ethylene is believed to proceed as shown in the following Table A:

TABLE A

| Step | Reaction type | Reaction |
|---|---|---|
| 1 | Initiation | DTBP + Δ → 2 TBP* |
| 2 | Initiation | TBP* + $CH_3CH_2OH$ → *$CH(CH_3)OH$ + TBuOH |
| 3 | Propagation | *$CH(CH_3)OH$ + $CH_2=CH_2$ → *$CH_2CH_2CH(CH_3)OH$ |
| 4 | Propagation (chain transfer) | *$CH_2CH_2CH(CH_3)OH$ + $CH_3CH_2OH$ → *$CH(CH_3)OH$ + $CH_3CH_2CH(CH_3)OH$ |
| 5 | Propagation (chain extension) | *$CH_2CH_2CH(CH_3)OH$ + n $CH_2=CH_2$ → *$(CH_2CH_2)_{n+1}CH(CH_3)OH$ |
| 6 | Propagation (chain transfer) | *$(CH_2CH_2)_{n+1}CH(CH_3)OH$ + $CH_3CH_2OH$ → $H(CH_2CH_2)_{n+1}CH(CH_3)OH$ + *$CH(CH_3)OH$ |
| 7 | Termination: In 7a two radicals combine. In 7b two radicals disproportionate, resulting in two neutral non-radical products. | a. Radical combination, any *R + *R' → R—R' b. Radical disproportionation, e.g. 2*$CH(CH_3)OH$ → $CH_3CH_2OH$ + $CH_3CHO$ |

TABLE A-continued

| Step | Reaction type | Reaction |
|---|---|---|
| | Each is a different terminating step. | |

According to Table A, a C1 to C12 telogen (ethanol as illustrated) and ethylene are reacted to form a telomer product mixture. The molar ratio of the ethanol to the ethylene as supplied is greater than 4:1. In step 1, heat causes the initiator DTBP to generate two radical species that help to initiate an additional initiation step and a plurality of propagation steps. The ethanol is used to provide a corresponding ethanol radical *$CH(CH_3)OH$. This occurs when the TBP* radicals react with ethanol to produce ethanol radicals in Step 2. In Step 3, the ethanol radical then reacts with ethylene to provide a chain extended, radical intermediate *$CH_2CH_2CH(CH_3)OH$. The chain extended, radical intermediate then reacts in two different ways according to Steps 4 and 5. In step 4, the chain extended, free radical intermediate reacts with a C1 to C12 telogen (ethanol in this embodiment) to provide a first chain extended, terminated reaction product $CH_3CH_2CH(CH_3)OH$ and an additional amount of ethanol radical species. In Step 5, the chain extended, free radical intermediate reacts with ethylene to produce a further chain extended free radical intermediate *$(CH_2CH_2)_{n+1}CH(CH_3)OH$, wherein n is as defined above. The mixture of chain extended, radical intermediates then reacts with ethanol in step 6 to prepare a mixture of telomer products $H(CH_2CH_2)_{n+1}CH(CH_3)OH$ and additional ethanol radicals. Steps 7a, 7b constitutes a termination steps. Desirably, steps 1 through 7a occur in a reaction in which contact between metal materials and the reaction medium is minimized or avoided. This is because metal surface may promote undesirable disproportionation 7b through electron transfers.

In Table A, steps 4 and 6 are chain transfer steps and are important aspects so that the reaction is selective for providing lower molecular weight telomers for which n has a weight average value in the range from 1 to 20, preferably 1 to 10, more preferably 1 to 5, even more preferably 1 to 3. It is desirable for step 3 to occur at least 20 times per each step 2. This is accomplished by using a limited amount of initiator as described herein. The intermediate product of step 3 may undergo either step 4 or step 5. It is desirable for step 4, a chain transfer step, to occur more frequently than step 5. This is accomplished by using a stoichiometric excess of the ethanol and desirably by running the reaction continuously and in the liquid phase and at high rate as described herein. This process desirably maintains a steady state concentration of ethylene in the reaction zone much lower than fed and thereby results in a very high telogen to ethylene ratio at all times. In the case of ethanol this means *$CH_2CH_2CH(CH_3)OH$ radical (1:1 adduct of ethylene and ethanol radical) has a higher relative statistical probability of encountering an ethanol molecule for chain transfer rather than an ethylene molecule for chain extension, than one would expect based on the feed ratio of telogen to taxogen. More over this enhancement of chain transfer probability over chain extension also applies in general to other telomer radicals, *$(CH_2CH_2)_{n+1}CH(CH_3)OH$ in the reaction zone. The net impact is the probability of reaction 4 and 6 is enhanced relative to chain extension reaction 5. The relative availability of ethylene (feed concentration and reaction zone concentration), reaction pressure, and starting monomer and to some degree reaction temperature help to control the product mixture and degree of chain extension. In summary, applying the principles of the invention allows telomers of much more limited degree and of less broad molecular weight than was previously possible. In fact it is possible in many cases for the 1:1 telogen to taxogen product to be the one produced in highest percentage. Analogous reaction sequences may occur with propylene, ethylene/propylene mixtures or with other alcohols/hydrocarbons.

An important aspect of this pathway is the maximizing of propagation relative to termination to the degree that the economic cost of the peroxide becomes irrelevant. This is accomplished at least in part by excluding or minimizing the contact of the reaction medium with metal materials. The ratio of reaction step 4 to reaction step 5 is defined in the prior art as the chain transfer efficiency. It is reported that low chain transfer efficiencies on the order of about $10^{-2}$ are typical for reactions between ethylene and ethanol and further that telomerization would not be expected to yield primarily low molecular weight products, where n on a weight average basis is 1 to 5 or even 1 to 3. See "Free Radicals" Volume II Edited by Jay K. Kochi, 1973 or Reference 4-"Free Radical Telomerization" Edited by Charles Stark 1974. Therefore, the present invention overcomes this bias to provide a reaction strategy that is selective for the lower molecular weight products.

The principles of the present invention can be used to make fuels from ethylene and/or propylene. In one example, ethylene and/or propylene can be reacted with one or more C1 to C6 alcohols in order to make C3 to C15 alcohol functional telomers. All or a portion of the alcohols can be dehydrated to hydrocarbons useful as fuel. Some fuel formulations favor high oxygen content. Accordingly, all or a portion of the C3 to C15 alcohols could be incorporated into fuel formulations without dehydration if desired. In another example, ethylene and/or propylene can be reacted with one or more C3 to C12 hydrocarbons in order to make C5 to C24 telomers. These telomers, if desired, could be used directly in fuel. The principles of the present invention can also be used to make propylene, propanol or other desired chemicals in part or totally independent of fuel.

The present invention will now be further described with reference to the following illustrative examples.

Example 1

A gaseous stream containing 94.3 wt % (about 89 mole %) isobutane, 0.09 wt % DTBP and 5.6 wt % (about 11 mole %) ethylene is preheated in an inert surface zone and is fed to a Teflon lined tubular reactor zone maintained at minimum temperature of 135° C. and with a back pressure of 100 psig using a back pressure regulator. The reaction system is configured with a top to bottom flow. The feed rate and temperature are adjusted so as to provide about 90% conversion of the contained ethylene. The effluent is chilled under pressure to give a liquid product. The liquid product contains in addition to isobutane contains about 10% of C6, C8, C10, C12 and C14 telomer products. The weight ratio of the total amount of telomer products to DTBP is greater than 60.

Example 2

A PTFE(Teflon)-lined, 300 cc autoclave equipped with an internal Teflon stirrer, and Teflon coated internals (ethylene feed tube and thermo well) was evacuated under mild vacuum and purged twice with nitrogen. The reactor was equipped with a preheated liquid feed line, an ethylene feed line and a reactor over flow line which is routed to a liquid product Hoke collection vessel equipped with a back pressure regulator. The resulting reactor having an internal volume of about 240 ml is charged with 200 g of isopropanol and pressurized with nitrogen, while setting the back pressure to 350 psi. A nitrogen blanketed liquid feed tank is charged with 1200 g of isopropyl alcohol containing 1.08 g (0.09%) of ditertiary butyl peroxide (DTBP). The reactor is brought to about 160° C. Ethylene flow (about 104 sccm, 4.7 mmol per minute) and liquid isopropyl alcohol/DTBP feed (about 6.1 ml per minute, (80 mmol per minute) were initiated. The reactor contents gradually rose in temperature to about 173° C. The run was conducted for approximately 4.5 hours with the conditions and composite liquid product samples taken about every 45 minutes from the Hoke collection vessel as shown in the following table:

Isopropyl Alcohol/Ethylene Run Table

| Run Time Minutes | Process Temperature ° C. | Ethylene Feed sccm | Ethylene Feed mmol/minute | IPA/DTBP Solution Feed Rate ml/minute | IPA mmol/minute | Sample # | Sample Wt g |
|---|---|---|---|---|---|---|---|
| -5 | 158 | 104 | 4.7 | 0.0 | 0 | | |
| 0 | 162 | 104 | 4.7 | 7.1 | 93 | 1 | 21 |
| 15 | 165 | 104 | 4.7 | 6.0 | 79 | | |
| 45 | 173 | 104 | 4.7 | 6.0 | 79 | 2 | 253 |
| 60 | 172 | 104 | 4.7 | 6.0 | 79 | | |
| 90 | 174 | 104 | 4.7 | 6.1 | 80 | 3 | 224 |
| 105 | 173 | 104 | 4.7 | 6.2 | 81 | | |
| 135 | 174 | to 75 | 3.3 | 6.2 | 81 | 4 | 225 |
| 150 | 174 | 75 | 3.3 | 6.2 | 81 | | |
| 180 | 175 | 75 | 3.3 | 6.2 | 81 | 5 | 222 |
| 195 | 173 | 75 | 3.3 | 6.2 | 81 | | |
| 225 | 173 | to 171 | 7.6 | 6.2 | 81 | 6 | 214 |
| 240 | 175 | 171 | 7.6 | 6.2 | 81 | | |
| 270 | 177 | 171 | 7.6 | 6.2 | 81 | 7 | 232 |

The ethylene conversion was calculated to be over 80% in all samples. The product sample gas chromatography analysis is shown in the following product table. Note the C5, C7, C9, C11, C13, C15, & C17 alcohols are formed from 1 molecule of IPA and 1-7 molecules of ethylene, respectively. The number, n, of molecules of ethylene incorporated into the alcohols also is known as the degree of chain extension. In this example, the reactor has a volume of 240 ml while the feed is introduced at 6 ml/min. This provides 40 minutes residence time. The steady state conditions of this example provide high conversion of taxogen but lower conversion of telogen. Consequently, the ethylene steady state concentration in the reaction zone is less than the concentration of ethylene in the feed. These conditions favor multiple occurrences of chain transfer steps. The ability to accomplish this is greatly facilitated by using a reaction vessel with inert surfaces.

IPA/Ethylene GC Sample Analysis

| Sample | Wt % Alcohols | | | | | | | C19 + C21 | Total C5- C17 | Wt Ratio Alcohols to Initiator | Selectivity 1 C5/C Total | Selectivity 2 C5 + C7/ C Total |
|---|---|---|---|---|---|---|---|---|---|---|---|---|
| | C5 | C7 | C9 | C11 | C13 | C15 | C17 | | | | | |
| 2 | 1.95 | 0.78 | 0.37 | 0.15 | 0.06 | 0.02 | 0.01 | 0 | 3.34 | ? | 58% | 82% |
| 3 | 3.93 | 1.74 | 0.89 | 0.37 | 0.16 | 0.07 | 0.03 | 0.01 | 7.20 | 90 | 55% | 79% |
| 4 | 4.23 | 1.86 | 0.94 | 0.39 | 0.17 | 0.07 | 0.03 | 0.01 | 7.70 | 96 | 55% | 79% |
| 5 | 4.67 | 1.95 | 0.93 | 0.36 | 0.14 | 0.06 | 0.02 | 0.01 | 8.14 | 102 | 57% | 82% |
| 6 | 4.97 | 1.89 | 0.83 | 0.29 | 0.11 | 0.04 | 0.01 | 0 | 8.14 | 102 | 61% | 84% |
| 7 | 4.26 | 1.87 | 0.95 | 0.40 | 0.18 | 0.08 | 0.04 | 0.02 | 7.8 | 98 | 55% | 79% |

Reactor Residence Time = ~40 minutes.

Example 3

The reactor system of Example 2 having an internal volume of about 240 ml was charged with 200 g of ethanol about 1% mixed heptanes denatured) and pressurized with nitrogen, while setting the back pressure to 800 psi. A nitrogen blanketed liquid feed tank is charged with 1280 g of ethanol containing 1.55 g (0.12%) of ditertiary butyl peroxide (DTBP). The reactor is brought to about 167° C. Ethylene flow (about 104 sccm, 4.7 mmol per minute) and liquid ethanol/DTBP feed (about 6.0 ml per minute, about 102 mmol per minute) were initiated. The reactor contents gradually rose in temperature to about 185° C. The run was conducted for approximately 4.5 hours with the conditions and composite liquid product samples taken about every 45 minutes from the Hoke collection vessel as shown in the following table:

Ethanol/Ethylene Run Table

| Run Time Minutes | Process Temp. °C. | Ethylene Feed sccm | ~Ethylene Feed mmol/minute | EtOH/DTBP Solution Feed Rate ml/minute | ~EtOH mmol/minute | Sample # | Sample Wt g |
|---|---|---|---|---|---|---|---|
| 0 | 167 | 104 | 4.7 | 5.0 | 84 | | |
| 10 | 169 | 104 | 4.7 | 5.3 | 88 | 1 | 80 |
| | | 104 | 4.7 | 6.0 | 102 | | |
| 55 | 185 | 104 | 4.7 | 6.0 | 102 | 2 | 262 |
| | | 104 | 4.7 | 6.0 | 102 | | |
| 100 | 187 | 104 | 4.7 | 6.0 | 102 | 3 | 230 |
| | | 104 | 4.7 | 6.0 | 102 | | |
| 145 | 186 | 104 | 4.7 | 6.0 | 102 | 4 | 216 |
| | | 104 | 4.7 | 6.0 | 102 | | |
| 190 | 187 | 220 | 10 | 6.0 | 102 | 5 | 225 |
| | | 220 | 10 | 6.0 | 102 | | |
| 235 | 193 | 220 | 10 | 6.0 | 102 | 6 | 240 |
| | | 220 | 10 | 6.0 | 102 | | |
| 280 | 192 | 220 | 10 | 6.0 | 102 | 7 | 186 |
| | | | | | | 8 | 80 |

Used 1.55 g of DTBP dissolved in 1280 g ethanol (0.12%). Note the ethanol contained ~1% mixed heptanes as denaturant. The reaction back pressure was maintained ~800 psi.

The product sample gas chromatography analysis is shown in the table below. Note the C4, C6, C8, C10, C12, C14 & C16 alcohols are formed from 1 molecule of ethanol and 1-7 molecules of ethylene, respectively. In all samples over 50% of the secondary alcohol product resulted from the addition of 1 or 2 moles of ethylene per mole of ethanol. The C4 alcohol (2-butanol) was the major product in all samples. The total other alcohols are composed of products formed from addition of ethylene to the product alcohols as well as some higher molecular weight alcohols.

Ethanol/Ethylene GC Sample Analysis

| | Wt % Alcohols | | | | | | | | | | | |
|---|---|---|---|---|---|---|---|---|---|---|---|---|
| | Secondary Alcohols | | | | | | | | | Wt | Selectivity | Selectivity |
| Sample | C4 | C6 | C8 | C10 | C12 | C14 | C16 | Total C4-C16 | Total Other OH? | Total ROH | Ratio Alcohols to Initiator | C4/C Total 2° ROH | C4-C6/C Total 2° ROH |
| 2 | 0.92 | 0.31 | 0.22 | 0.12 | 0.07 | 0.04 | 0.03 | 1.71 | 0.69 | 2.40 | 20 | 54% | 72% |
| 3 | 1.32 | 0.59 | 0.48 | 0.29 | 0.2 | 0.14 | 0.09 | 3.11 | 1.41 | 4.52 | 38 | 43% | 60% |
| 4 | 1.28 | 0.60 | 0.50 | 0.32 | 0.22 | 0.16 | 0.10 | 3.18 | 1.60 | 4.78 | 40 | 40% | 59% |
| 5 | 1.28 | 0.60 | 0.50 | 0.32 | 0.22 | 0.16 | 0.10 | 3.18 | 1.40 | 4.58 | 38 | 40% | 59% |
| 6 | 1.21 | 0.59 | 0.51 | 0.33 | 0.23 | 0.17 | 0.11 | 3.15 | 1.60 | 4.75 | 40 | 39% | 58% |
| 7 | 1.14 | 0.57 | 0.50 | 0.33 | 0.24 | 0.18 | 0.12 | 3.08 | 1.38 | 4.46 | 37 | 37% | 56% |
| 8 | 1.27 | 0.72 | 0.68 | 0.46 | 0.34 | 0.26 | 0.18 | 3.910 | 2.200 | 6.110 | 51 | 33% | 50% |

Reactor Residence Time = ~40 minutes. Used 1.60 g (0.12%) DTBP Translates to 0.038 mmol per minute Example 4

The experiment of Example 3 is repeated using methanol as the feed alcohol instead of ethanol. N-propanol is the product in highest percentage yield.

All patents, patent applications, and publications cited herein are incorporated by reference in their respective entireties for all purposes. The foregoing detailed description has been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of using ethylene and/or propylene taxogen to prepare one or more higher molecular weight compounds, comprising the step of free radically reacting reactants comprising ethylene and/or propylene taxogens and at least one C1 to C12 telogen in the presence of a free radical initiator component, wherein:
    a. the at least one C1 to C12 telogen and the ethylene and/or propylene taxogens are supplied to a reaction zone at a feed molar ratio of the telogens to the taxogens that is in the range from 2:1 to 200:1;
    b. the ethylene and/or propylene taxogens and the free radical initiator component are supplied to the reaction zone at a molar ratio of the ethylene and/or propylene taxogens to the free radical initiator component that is in the range from 8:1 to 10,000:1; and
    c. the at least one C1 to C12 telogen and the ethylene and/or propylene taxogens are present in the reaction zone at a steady state molar ratio of the telogens to the taxogens that is at least twice the feed molar ratio of the telogens to the taxogens.

2. The method of claim 1, wherein
    the at least one C1 to C12 telogen and the ethylene and/or propylene taxogens are present in the reaction zone at a steady state molar ratio of the telogens to the taxogens that is in the range from 10:1 to 500:1.

3. The method of claim 1, wherein the reaction occurs continuously in a liquid phase.

4. The method of claim 1, wherein the ethylene and/or propylene taxogens are present in the reaction zone at a steady state concentration of 0.5 mole % to 3 mole % based on the total moles of steady state reactants in the reaction zone, and wherein the molar ratio of ethylene and/or propylene taxogens to the free radical initiator component as supplied to the reaction zone is in the range from 40:1 to 1000:1.

5. The method of claim 1, wherein the reaction provides a product mixture and wherein a selected portion of the product mixture is recycled to the reaction zone.

6. The method of claim 1, wherein the reaction is carried out in the substantial absence of metal materials contacting the reactants in the reaction zone.

7. The method of claim 1, wherein the ethylene and/or propylene taxogens comprise ethylene that is supplied as a mixture comprising ethylene and ethane.

8. The method of claim 1, wherein the ethylene or propylene taxogens comprise ethylene and the method further comprises the steps of deriving the ethylene from ethanol and supplying the derived ethylene to the reaction zone.

9. The method of claim 1, wherein at least one C1 to C12 telogen comprises a heteroatom.

10. The method of claim 1, wherein the free radical initiator component comprises DTBP and/or TBHP.

11. The method of claim 1, wherein the reaction occurs in a reaction zone comprising a quartz surface, a ceramic surface, or a fluoropolymer surface.

12. The method of claim 1, wherein the reaction occurs in the substantial absence of oxygen gas.

13. The method of claim 1, wherein:
    a. the feed molar ratio is in the range from 8:1 to 100:1;
    b. the molar ratio of ethylene and/or propylene taxogens to the free radical initiator component as supplied to the reaction zone is in the range from 20:1 to 2000:1; and
    c. the steady state molar ratio is in the range from 24:1 to 250:1.

14. The method of claim 1, wherein the reaction occurs at a temperature in the range from 100° C. to 300° C. and at a pressure in the 400 psig to 4000 psig range.

15. The method of claim 1 wherein the at least one telogen comprises one or more alcohols.

16. The method of claim 1, wherein the at least one telogen comprises one or more hydrocarbons.

17. The method of claim 15, wherein the one or more alcohols comprise ethanol and/or methanol and wherein:
    a. the reaction occurs at a temperature in the range from 150° C. to 250° C.;
    b. the reaction zone is at a pressure is in the range from 300 psig to 2000 psig; and
    c. the feed molar ratio is in the range from 8:1 to 100:1;
    d. the molar ratio of ethylene and/or propylene taxogen to the free radical initiator component as supplied to the reaction zone is in the range from 40:1 to 2000:1; and
    e. the steady state molar ratio is in the range from 20:1 to 250:1 range.

18. The method of claim 15, wherein the one or more alcohols comprise one or more of methanol, ethanol, isopropanol, isobutanol, 1-butanol and/or 2-butanol.

19. The method of claim 16, wherein:
    a. the reaction occurs at a temperature in the range from 150° C. to 250° C.;
    b. the reaction zone is at a pressure is in the range from 300 psig to 2000 psig; and
    c. the reaction is carried out in the substantial absence of metal materials contacting the reactants in the reaction zone.

20. The method of claim 16, wherein a major portion of the prepared higher molecular weight products incorporate 1 to 3 moles of ethylene and/or propylene taxogen per mole of telogen.

21. The method of claim 1, wherein a major portion of the prepared higher molecular weight products incorporate 1 to 3 moles of ethylene and/or propylene taxogen per mole of telogen.

* * * * *